US012059684B2

(12) United States Patent
Li et al.

(10) Patent No.: US 12,059,684 B2
(45) Date of Patent: Aug. 13, 2024

(54) CONCENTRATING-ENRICHING MAGNETIC BEAD PURIFIER

(71) Applicant: The Emerther Company, Jiashan (CN)

(72) Inventors: Yongmei Li, Jiashan (CN); Li Li, Jiashan (CN); Lianhao Zhao, Jiashan (CN)

(73) Assignee: The Emerther Company, Jiaxing (CN)

( * ) Notice: Subject to any disclaimer, the term of this patent is extended or adjusted under 35 U.S.C. 154(b) by 830 days.

(21) Appl. No.: 17/250,217

(22) PCT Filed: Jun. 26, 2019

(86) PCT No.: PCT/CN2019/093092
§ 371 (c)(1),
(2) Date: Dec. 16, 2020

(87) PCT Pub. No.: WO2020/001493
PCT Pub. Date: Jan. 2, 2020

(65) Prior Publication Data
US 2021/0254045 A1 Aug. 19, 2021

(30) Foreign Application Priority Data

Jun. 26, 2018 (CN) .......................... 20180993578.5

(51) Int. Cl.
*C07K 1/14* (2006.01)
*B01L 3/00* (2006.01)

(52) U.S. Cl.
CPC ............ *B01L 3/50855* (2013.01); *C07K 1/14* (2013.01); *B01L 2200/0668* (2013.01);
(Continued)

(58) Field of Classification Search
CPC ......... B01L 3/50855; B01L 2200/0668; B01L 2300/0609; B01L 2300/0829;
(Continued)

(56) References Cited

U.S. PATENT DOCUMENTS

| | | | | |
|---|---|---|---|---|
| 4,271,123 A | * | 6/1981 | Curry ................. | G01N 33/5302 436/805 |
| 2008/0171337 A1 | * | 7/2008 | Miyazaki ........... | C12N 15/1013 435/283.1 |

(Continued)

*Primary Examiner* — Matthew D Krcha
*Assistant Examiner* — Sophia Y Lyle
(74) *Attorney, Agent, or Firm* — Wang Law Firm, Inc.

(57) ABSTRACT

A concentrating-enriching magnetic bead purifier includes a base, at least one first mixing sleeve socket, at least one second mixing sleeve socket, and a plurality of wells, and a controlling module. The first mixing sleeve socket includes a first magnetic rod, and a first magnetic rod sleeve. The second mixing sleeve socket includes a second magnetic rod and a second magnetic rod sleeve. A diameter of a cross section of the second magnetic rod sleeve is smaller than that of the first magnetic rod sleeve. The wells include at least one binding well, at least one washing well, and at least one elution well. The volume of the elution well is smaller than that of the binding well. The controlling module controls the first magnetic rod sleeve to only mix or adsorb in the binding well and the washing well and controls the second magnetic rod sleeve to mix or adsorb in the washing well and the elution well.

9 Claims, 5 Drawing Sheets

(52) U.S. Cl.
CPC ............. *B01L 2300/0609* (2013.01); *B01L 2300/0829* (2013.01); *B01L 2400/043* (2013.01)

(58) Field of Classification Search
CPC ....... B01L 2400/043; C07K 1/14; C07K 1/22; G01N 2035/00564; G01N 1/34; G01N 1/4077; G01N 35/0098; B01F 31/441; B01F 33/813; C12N 15/1013
See application file for complete search history.

(56) References Cited

U.S. PATENT DOCUMENTS

| | | | | |
|---|---|---|---|---|
| 2010/0288705 | A1* | 11/2010 | Griebel | G01N 35/10 210/695 |
| 2011/0147294 | A1* | 6/2011 | Fritchie | B03C 1/286 210/222 |
| 2012/0309104 | A1* | 12/2012 | Uematsu | B01L 3/0275 436/174 |

* cited by examiner

Prior art

Prior art

CONCENTRATING-ENRICHING MAGNETIC BEAD PURIFIER

BACKGROUND

1. Technical Field

The present invention relates to an equipment for rapid and efficient purification of biology specimen, and more particularly to a concentrating-enriching magnetic bead purifier.

2. Description of the Related Art

As the carrier of genetic information, nucleic acids are the material basis of gene expression. In addition to their important role in normal growth, development, and reproduction of organisms, nucleic acids are closely related to unusual circumstances of the life, such as tumor development, radiation injury, and genetic diseases, etc. Therefore, extraction and purification of nucleic acids is an essential process in molecular biology and medical research. In work of clinical diagnosis and treatment, or forensic identification, or genetic screening and recombination, the nucleic acids need to be extracted from specimen, such as blood, saliva, other tissues, and so on at first. The process of extracting nucleic acids is also called nucleic acid purification. The effectiveness of the nucleic acid purification directly affects the progress and results of medical research and diagnoses. Therefore, nucleic acid purification technology is very important in biotechnology.

A common nucleic acid purifying method is magnetic rod method. It uses a magnetic rod to adsorb magnetic beads and the magnetic beads are used to bind nucleic acids so as to separate nucleic acids from the specimen. In the process of separation, the biological specimen is lysed at first and bound onto the magnetic beads. And then, the bound substance is washed and purified to remove impurities so as to obtain purified nucleic acids. The magnetic rod method is generally divided into a plurality of steps, such as lysis, binding, washing, elution etc. The transition between steps is finished by fully mixing the magnetic beads and the solution, binding nucleic acids onto the magnetic beads and removing non-specific impurities without the action of magnetic field, and enriching and transferring the magnetic beads under the action of magnetic field. As shown in FIG. 1, the working principle of the magnetic rod method is explained. A magnetic rod 20, a mixing sleeve 21 and a deep-well plate 22 are arranged from top to bottom. The deep-well plate 22 is provided with a set of deep wells and the deep wells are divided into lysis solution wells 221, magnetic bead wells 222, washing solution wells 223 (multiple washing solution wells can be set up simultaneously), and elution wells 224, and they are used to store corresponding reagents. The specific steps of the nucleic acid purifying process includes: adding specimen into a lysis solution to release the nucleic acids; collecting the magnetic beads and placing them into the lysis solution wells 221; binding the magnetic beads and the nucleic acids; collecting the magnetic beads again and placing them into the washing solution wells 223 (can wash multiple times); collecting the magnetic beads thirdly and placing them into the elution wells 224; and retrieving the magnetic beads after elution. Finally, the nucleic acids remain in the eluate. In order to facilitate the automation of the above process, the nucleic acid purifier shown in FIG. 1 is required to achieve the following basic step: (a) up and down movement of the magnetic rod 20; (b) up and down movement and stirring action of the mixing sleeve 21; (c) up and down movement of the mixing sleeve 21 after the magnetic rod 20 is inserted therein; (d) translational motion of the mixing sleeve after the magnetic rod 20 is inserted therein.

Currently, the common nucleic acid purifiers generally use container of the same volume to store various solutions and they are suitable for extracting nucleic acids from small-volume liquid specimen (50-400 microliters). When larger container (4-10 ml) and large diameter magnetic rod are used to extract the nucleic acids, the minimum volume of the eluting solution is usually large (about 100-300 microliters) due to the limitation of magnetic rod's large diameter. However, in certain circumstances, it is necessary to extract trace amounts of nucleic acids from a larger volume of liquid specimen, such as liquid biopsy, viral nucleic acid hypersensitivity detection, and so on. In above cases, the magnetic beads need to bind nucleic acids in the larger volume of liquid specimen. And then the nucleic acids bound by the magnetic beads are washed to remove impurities. Finally, a small volume of eluting solution is used to elute the nucleic acids for subsequent detection. For example, for liquid biopsy and other projects, it is usually necessary to extract nucleic acids from 2-5 ml plasma specimen. That is to say, the magnetic beads bind the nucleic acids which are contained in lysis solution of about 10 ml, and the nucleic acids are eluted in the eluate solution of 20-50 µl. At present, the nucleic acid purifier in the prior art cannot accomplish this task efficiently.

CN206956049U discloses a nucleic acid purifier. As shown in FIG. 2, the nucleic acid purifier includes a base 13, a socket translation device 7 and a bracket lifting device 8 arranged on the base 13 and used to drive the magnetic rod 20 and the mixing sleeve 21 for up and down movement or translation movement, and a mixing sleeve driver 6 provided on the base 13. The mixing sleeve driver 6 is used to drive the mixing sleeve 21 to move independently up and down so as to mix. However, the nucleic acid purifier only uses one set of magnetic rod 20 and mixing sleeve 21 for extracting a certain type of nucleic acids. Therefore, this mixing and stirring strength is weak, and the effect of complete lysis and release of nucleic acid substances and binding with the magnetic beads cannot be achieved under certain conditions.

In addition to nucleic acid extraction, the magnetic rod method can also be used for protein extraction and purification. That is to say, the magnetic rod is used to adsorb the magnetic beads and the magnetic beads bind the protein so as to separate the protein from specimen. A biological specimen for protein purification may or may not undergo a lysis step. The initial volume of some biological specimen is also very large, ranging from microliters to tens of liters. Therefore, it is necessary to use an instrument to bind protein from large-volume specimen by the magnetic beads and then elute the protein by a small volume of the eluate solution to achieve purification and enrichment. Similar to the above-mentioned nucleic acid extraction, the current magnetic bead purifier cannot efficiently purify large-volume protein specimen.

Therefore, it is necessary to provide a concentrating-enriching magnetic bead purifier which makes it possible to solve the above problem.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout two views.

DETAILED DESCRIPTION

The present application is illustrated by way of example and not by way of limitation in the figures of the accompanying drawings. It should be noted that references to "an" or "one" embodiment in this application are not necessarily to the same embodiment, and such references mean at least one.

Figure 1:
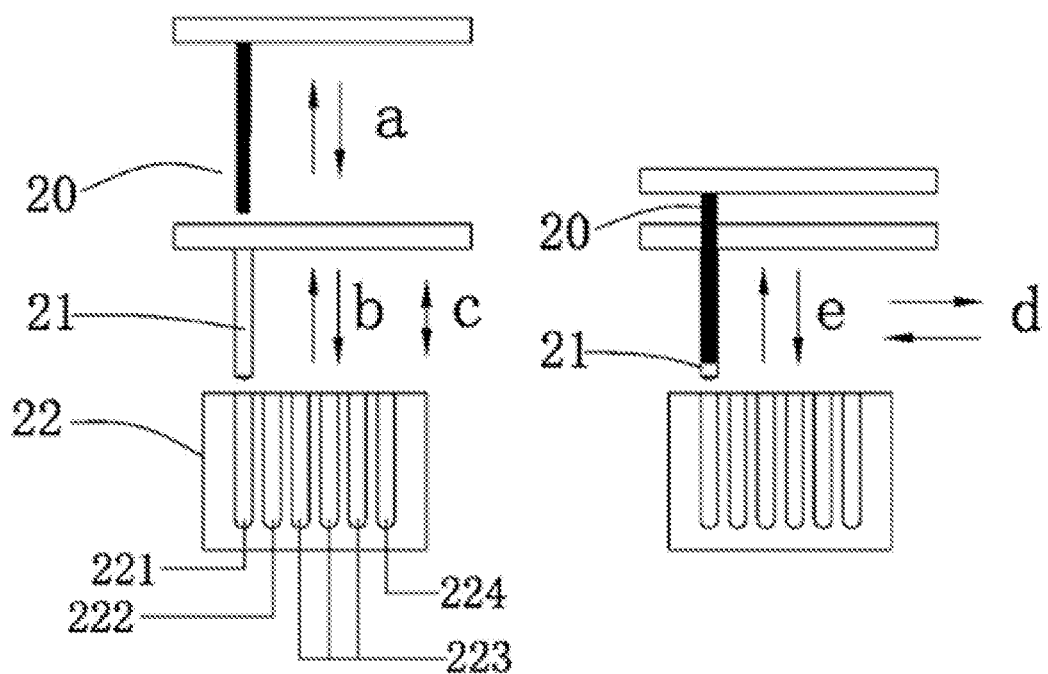
FIG. 1 is a work principle chart of a magnetic rod method in the prior art.
Figure 2:
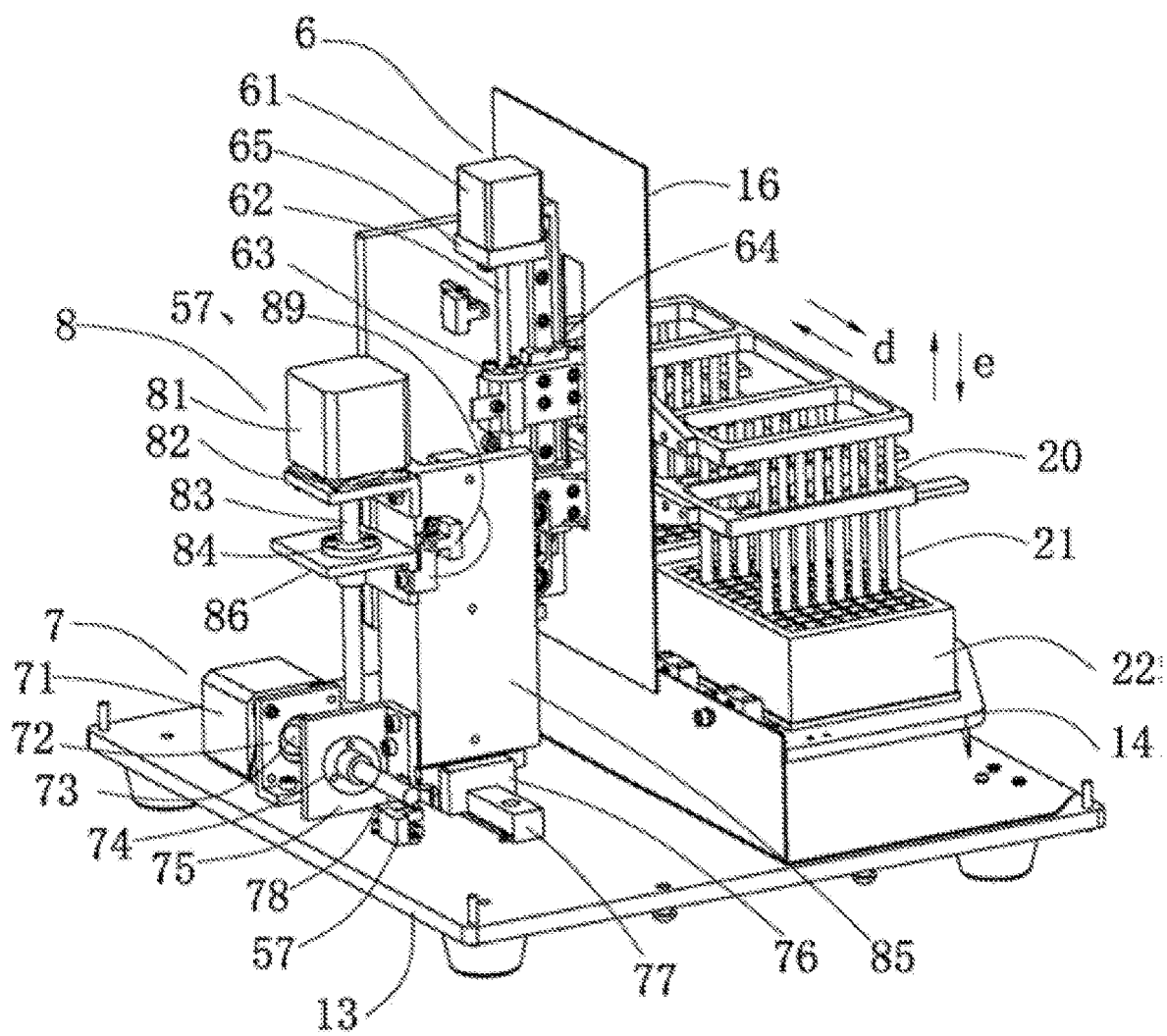
FIG. 2 is a schematic view of a nucleic acid purifier in the prior art.
Figure 3:
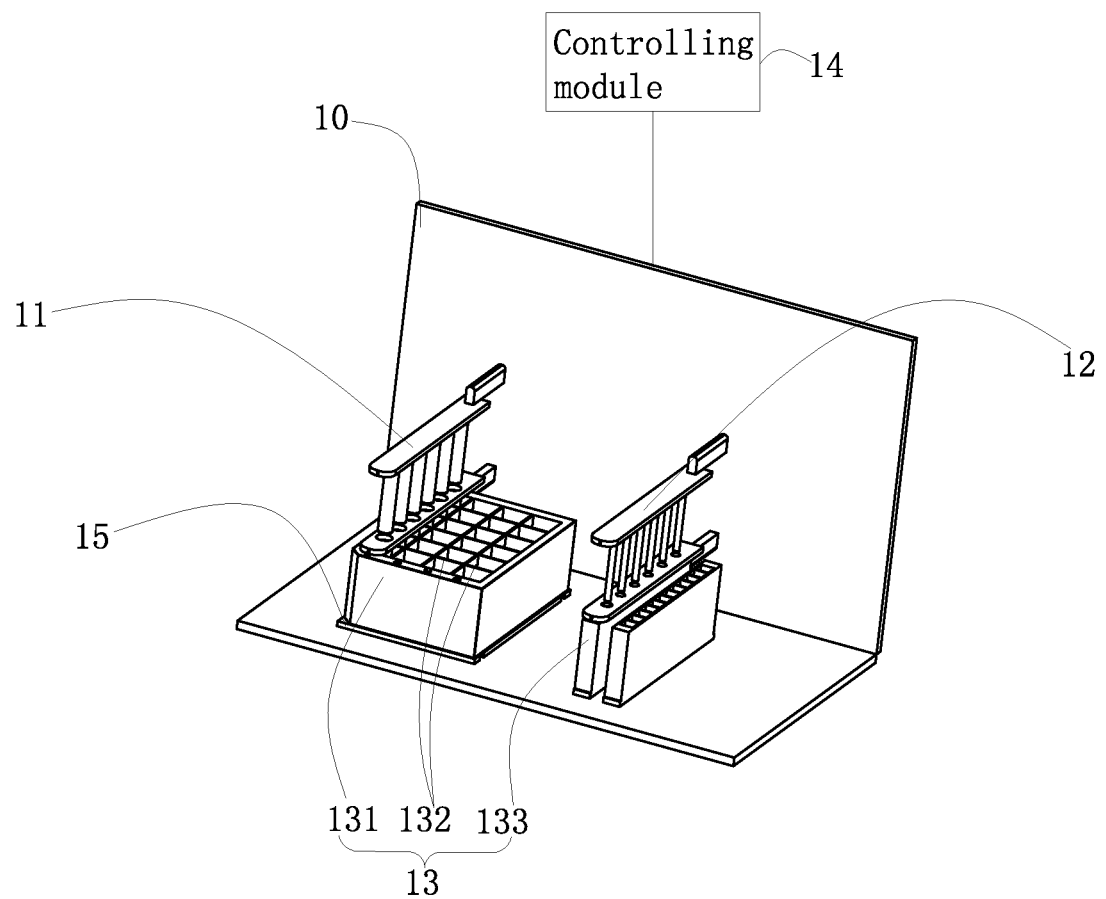
FIG. 3 is a schematic view of a concentrating-enriching magnetic bead purifier according to the present invention.
Figure 4:
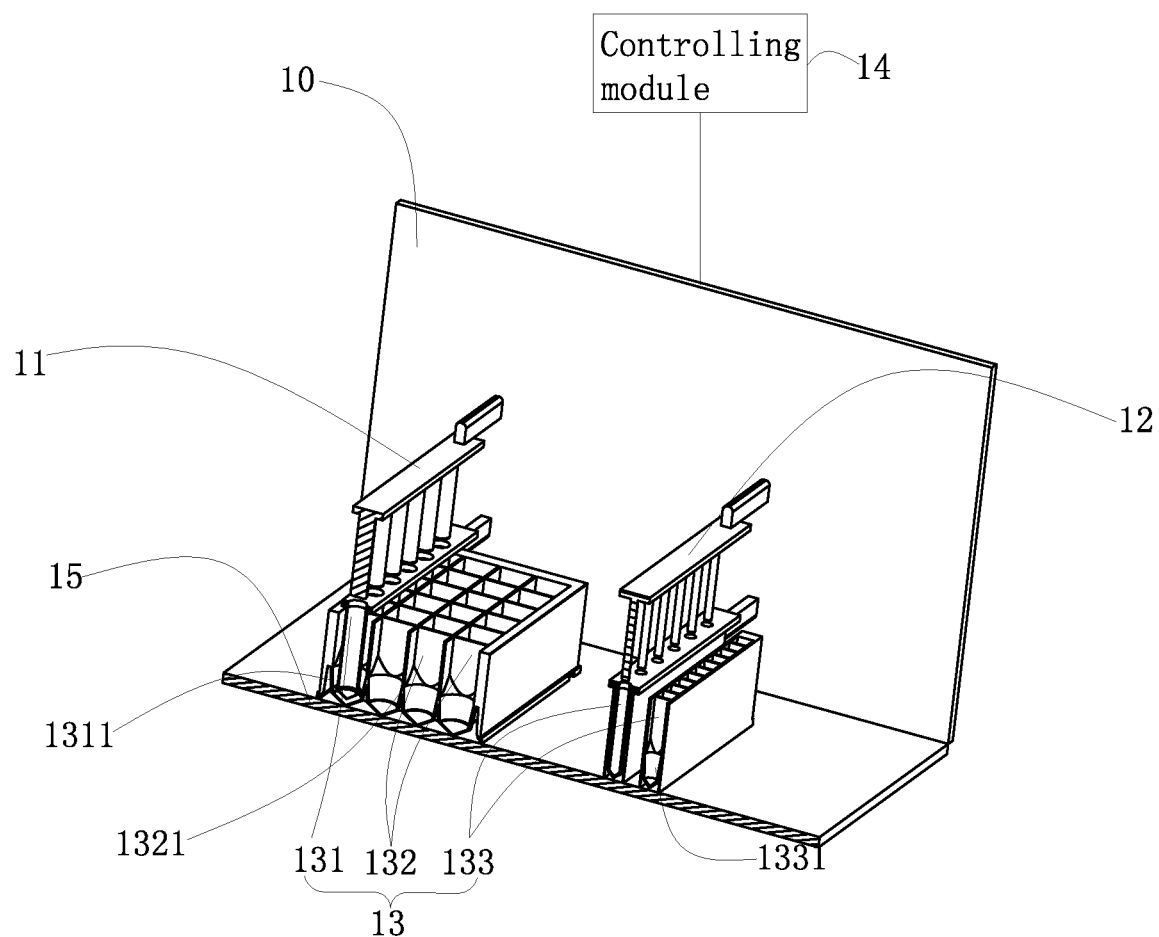
FIG. 4 is a section schematic view of the concentrating-enriching magnetic bead purifier of FIG. 3.
Figure 5:
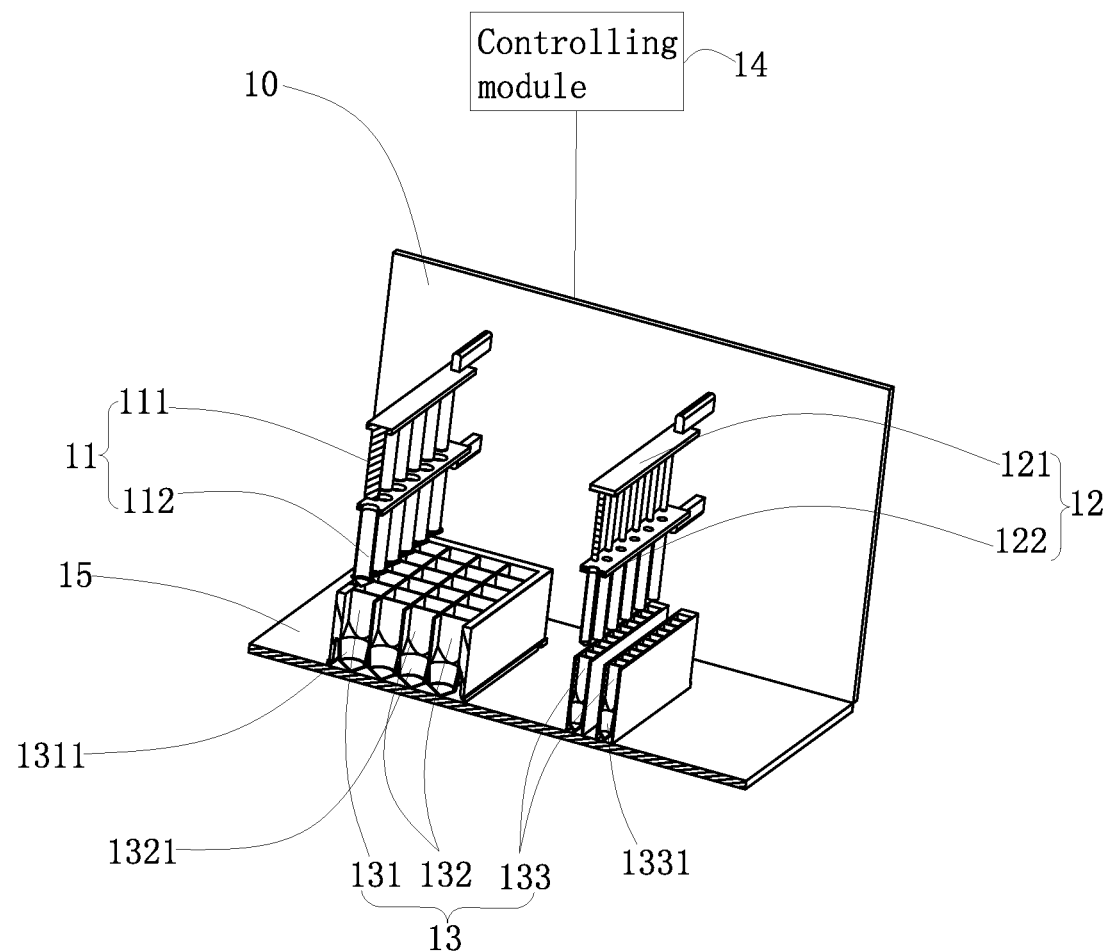
FIG. 5 is a schematic view of the concentrating-enriching magnetic bead purifier of FIG. 3.

Referring to FIG. 3 to FIG. 5, a concentrating-enriching magnetic bead purifier is shown in accordance with an exemplary embodiment of the present invention. Firstly, it is needed to explain that the concentrating-enriching magnetic bead purifier is used to extract and concentrate nucleic acids or proteins by magnetic beads. The extraction and concentration technology of the nucleic acids or the proteins itself is a prior art and does not require much explanation. The concentrating-enriching magnetic bead purifier includes a base 10, at least a first mixing sleeve socket 11 disposed on the base 10, at least a second mixing sleeve socket 12 disposed on the base 10, a plurality of wells 13 arranged on the base 10, and a controlling module 14 used for controlling the first mixing sleeve socket 11 and the second mixing sleeve socket 12. Understandably, the concentrating-enriching magnetic bead purifier further includes other functional components, such as bead transferring device and electric controlling device used to drive the first, second mixing sleeve socket 11, 12 to move up and down, assemble components, and install components, which should be some technique known to those skilled in the art, and will not be described in detail here.

The base 10 is constructed for disposing or installing various functional modules, such as, the above bead transferring device and the electric controlling device, assemble components, and the wells, and so on. The base 10 may have various structures and shapes to suit the installation and placement of various other devices.

The first mixing sleeve socket 11 is movably disposed on the base 10 and includes at least one first magnetic rod 111, and at least one first magnetic rod sleeve 112 arranged to insert the first magnetic rod 111 therein. Those skilled in the art should be known that the first mixing sleeve socket 11 should be shaken under the control of the independent horizontal and vertical movement device and the electric controlling device so as to mix the solution contained therein. The working principle of its shaken has been described in the patent CN206956049U and is not described in detail here. In use and when it needs to mix the solution contained in the well, only the first magnetic rod sleeve 112 is insert into the well 13 to mix the solution. Moreover, when it needs to absorb the magnetic beads, the first magnetic rod 111 is firstly inserted into the first magnetic rod sleeve 112, and then the first mixing sleeve socket 11 is inserted into the well 13 to adsorb the magnetic beads. Understandably, in order to improve working efficiency, the first magnetic rod 111 may be single or multiple, such as 1, 2, 3, 4, 6, 8, 12, 24, etc. Correspondingly, the first magnetic rod sleeve 112 should also have a single or multiple to correspond to the first magnetic rod 111.

The second mixing sleeve socket 12 has same construction and working principle with that of the first mixing sleeve socket 11 and is used to adsorb the magnetic beads. The second mixing sleeve socket 12 includes at least one second magnetic rod 121 disposed on the base 10, and at least one second magnetic rod sleeve 122 arranged to insert the second magnetic rod 121 therein. The difference between the second mixing sleeve socket 12 and the first mixing sleeve socket 11 is only that the cross section of the second magnetic rod 121 is different from that of the first magnetic rod 111. The cross sections of the second magnetic rod 121 and the second magnetic rod sleeve 122 are smaller than those of the first magnetic rod 111 and the first magnetic rod sleeve 112. The second magnetic rod 121 may be single or multiple, such as 1, 2, 3, 4, 6, 8, 12, 24, etc. Correspondingly, the second magnetic rod sleeve 122 should also have single or multiple to correspond to the second magnetic rod 121. The first magnetic rod 111 and the second magnetic rod 121 may have same size, and the first magnetic rod 111 or the second magnetic rod 121 cooperates with the first magnetic rod sleeve 112 and the second magnetic rod sleeve 122 to complete the enrichment and transfer of the magnetic beads.

More preferably, the first mixing sleeve socket 11 and the second mixing sleeve socket 12 can select different sizes and shapes according to the volume of specimen and the size and shape of the wells 13.

The well 13 is constructed for containing various types of specimen and includes at least one binding well 131, at least one washing well 132, and at least one elution well 133. The binding well 131 is used to hold a large volume of lysate or binding solution. In the binding well 131, the nucleic acids or protein are bound onto the magnetic beads. In order to obtain nucleic acids or protein as much as possible, the volume of the specimen and the lysate or the binding solution needs to be large enough in some cases. Some nucleic acids or protein can be purified without lysis and only the binding solution is required and no lysate is required. The washing well 132 is constructed for washing the nucleic acids or protein bound from the binding well 131 so as to purify them and remove impurities. As a result, the washing solution hold in the washing well 132 is also as much as possible. Therefore, the washing well 132 may have same volume with the binding well 131 or have smaller volume than the binding well 131. The elution well 133 is constructed for eluting the purified nucleic acids or protein from the magnetic beads and leave them in the eluate to form a sample that can be used for downstream testing or production preparation. Understandably, in order to achieve higher purity, each of the binding well 131, the washing well 132, and the elution well 133 may include multiple, such as, 1, 2, 3, or 4, 5, etc. Furthermore, in order to increase the concentration of nucleic acids or protein eluted in the elution well 133, the volume of the elution well 133 should be smaller than that of the binding well 131. In order to smoothly translate the first mixing sleeve socket 11 and the second mixing sleeve socket 12, heights of the binding well 131, the washing well 132, and the elution well 133 are preferably the same. Understandably, the heights of the binding well 131, the washing well 132, and the elution well 133 may be different by adjusting a height of a magnetic rod holder (not labeled). A maximum diameter of the elution well 133 should be smaller than that of the binding well 131. In actual use, the binding well 131, the washing well 132, and the elution well 133 cannot be filled up with the solution so as to avoid the liquid from overflowing after the first and second magnetic rod sleeves 112 and 122 are inserted. The binding well 131, the washing well 132, and the elution well 133 include respectively binding mixture part 1311, a washing mixture part 1321, and an elution mixture part 1331. The maximum volume of the liquid contained in the binding well 131 is 1 to 200 times that of the liquid contained in the washing well 132, and the maximum volume of the liquid contained in the binding well 131 is 2 times to 1000 times that of the liquid contained in the elution well 133 so as to achieve the maximum concentration and enrichment of nucleic acids or protein. In the present embodiment, the number of the well 13 matches that of the first and second mixing sleeve socket 11 and 12. To improve mixing and eluting outcomes, the maximum diameter of the cross section of the first magnetic rod sleeve 112 is greater than that of the elution mixing portion 1331 and that of the elution well 133. Understandably, if necessary, same specifications can be used for the binding well, the washing well, and the elution well. Therefore, a largest diameter of a cross section of the first magnetic rod sleeve 112 is equal to or smaller than that of the washing mixing part of some or all of the washing wells. And the largest diameter of a cross section of the first magnetic rod sleeve 112 can also be equal to or smaller than that of the elution well 133 and that of the elution mixing part 1331 of the elution well 133.

The controlling module 14 is constructed for controlling the bead transferring device and the electric controlling device to move up and down or left and right. It can be realized for the operating rules and parameters of bead transferring device and the electric controlling device under the control of computer programs, as disclosed in the patent CN206956049U, which should be the prior art and will not be repeated here. The controlling module 14 is used to control the first magnetic rod sleeve 112 to mix or adsorb only in the binding well 131 and the washing well 132, and to control the second magnetic rod sleeve 122 to mix and adsorb in the washing well 132 and the elution well 133. Moreover, if necessary, the second magnetic rod sleeve 122 can also be controlled to adsorb the magnetic beads contained in the binding well 131.

The concentrating-enriching magnetic bead purifier further includes at least one well holder 15. The well 13 is arranged on the well holder 15 to relative position thereof.

As above described, the concentrating-enriching magnetic bead purifier have the first and second mixing sleeve with different sizes, and the well 13 with different volumes. In actual use, the large volume liquid specimen is stored in the binding well 131 and the first mixing sleeve socket 11 is used to mix and adsorb. Since the cross section of the second magnetic rod sleeve 122 is smaller than that of the first magnetic rod sleeve 112, the second magnetic rod sleeve 122 can mix the magnetic beads in the washing well 132 and in the elution well 133 which has smaller volume. Therefore, the first magnetic rod 121 can adsorb the largest amount of nucleic acids or protein from the binding well 131 and the nucleic acids or protein is eluted from the magnetic beads and contained in the elution well 133 which has smaller volume. As a result, the concentrating-enriching magnetic bead purifier can maximize the concentration of the extracted nucleic acids or protein to meet the needs of detection or production preparation.

Further, the concentrating-enriching magnetic bead purifier can alone use the first mixing sleeve socket 11 or the second mixing sleeve socket 12 to complete the purification process including binding, washing, and elution.

In order to increase the number of extracted specimens, the concentrating-enriching magnetic bead purifier can also be equipped with multiple extraction devices which includes multiple binding wells, multiple washing wells, multiple elution wells, and multiple mixing sleeve sockets.

The concentrating-enriching magnetic bead purifier can also cooperate with the liquid workstation to complete the process from automatic dispensing to magnetic rod extraction and purification.

While the disclosure has been described by way of example and in terms of exemplary embodiment, it is to be understood that the disclosures is not limited thereto. To the contrary, it is intended to lamp shade various modifications and similar arrangements (as would be apparent to those skilled in the art). Therefore, the scope of the appended claims should be accorded the broadest interpretation so as to encompass all such modifications and similar arrangements.

What is claimed is:

1. A concentrating-enriching magnetic bead purifier, comprising:
   a base;
   at least one first mixing sleeve socket movably disposed on the base, the first mixing sleeve socket comprising at least one first magnetic rod provided on the base, and at least one first magnetic rod sleeve arranged to insert the first magnetic rod therein;
   at least one second mixing sleeve socket movably disposed on the base, the second mixing sleeve socket comprising at least one second magnetic rod provided on the base, and at least one second magnetic rod sleeve arranged to insert the second magnetic rod therein, a cross section area of the second magnetic rod sleeve being smaller than a cross section area of the first magnetic rod sleeve;
   a plurality of wells placed on the base, the wells comprising at least one binding well, at least one washing well, and at least one elution well, a volume of the elution well being smaller than that of the binding well; and
   a controlling module constructed for controlling the first mixing sleeve socket and the second mixing sleeve socket, the controlling module controlling the first magnetic rod sleeve to only mix or adsorb in the binding well and the washing well and controlling the second magnetic rod sleeve to mix or adsorb in the washing well and the elution well.

2. The concentrating-enriching magnetic bead purifier as claimed in claim 1, wherein the first mixing sleeve socket and the second mixing sleeve socket are constructed for mixing, enriching, and transferring magnetic beads.

3. The concentrating-enriching magnetic bead purifier as claimed in claim 2, wherein the controlling module controls the second mixing sleeve socket to mix in the washing well, adsorb the magnetic beads contained in the washing well, and transfer the magnetic beads to the elution well which has the same or smaller volume than the washing well.

4. The concentrating-enriching magnetic bead purifier as claimed in claim 2, wherein the first magnetic rod and the second magnetic rod have the same size, and the first magnetic rod and the second magnetic rod cooperates with the first magnetic rod sleeve and the second magnetic rod sleeve to complete the enrichment and transfer of the magnetic beads.

5. The concentrating-enriching magnetic bead purifier as claimed in claim 1, wherein the volume of the elution well is smaller than that of the binding well.

6. The concentrating-enriching magnetic bead purifier as claimed in claim 1, wherein each of the at least one elution well comprises an elution mixture part, a maximum diameter of the cross section area of the first magnetic rod sleeve is greater than that of the elution well and that of the elution mixture part.

7. The concentrating-enriching magnetic bead purifier as claimed in claim 1, wherein each of the at least one washing well comprises a washing mixture part, a largest diameter of the cross section area of the first magnetic rod sleeve is equal to or smaller than that of the washing mixture part of some or all of the washing wells.

8. The concentrating-enriching magnetic bead purifier as claimed in claim 1, wherein the concentrating-enriching magnetic bead purifier comprises a well holder arranged on the base, the plurality of wells is disposed in the well holder so as to fix it.

9. The concentrating-enriching magnetic bead purifier as claimed in claim 1, wherein a maximum volume of a liquid contained in the binding well is 1 to 200 times that of a liquid contained in the washing well, and a maximum volume of the liquid contained in the binding well is 2 times to 1000 times that of a liquid contained in the elution well.

* * * * *